(12) United States Patent
Schendel

(10) Patent No.: US 7,780,444 B1
(45) Date of Patent: Aug. 24, 2010

(54) ORTHODONTIC ANCHOR

(75) Inventor: Stephen A. Schendel, Menlo Park, CA (US)

(73) Assignee: Veris Medical, Inc., Menlo Park, CA (US)

( * ) Notice: Subject to any disclaimer, the term of this patent is extended or adjusted under 35 U.S.C. 154(b) by 186 days.

(21) Appl. No.: 12/006,773

(22) Filed: Jan. 7, 2008

(51) Int. Cl.
*A61C 3/00* (2006.01)
(52) U.S. Cl. ......................................... 433/18; 433/174
(58) Field of Classification Search .................. 433/18, 433/19, 20, 21, 24, 172, 173, 174, 175, 176; 411/400, 404
See application file for complete search history.

(56) References Cited

U.S. PATENT DOCUMENTS

| | | | |
|---|---|---|---|
| 6,354,834 B2 * | 3/2002 | Kanomi et al. ................ 433/18 |
| 6,669,473 B1 | 12/2003 | Maino | |
| 6,761,521 B2 * | 7/2004 | McCormack et al. ........ 411/353 |
| 7,172,416 B2 * | 2/2007 | Lin .............................. 433/18 |
| 2004/0152035 A1 * | 8/2004 | Bumann et al. ............... 433/18 |
| 2005/0227197 A1 | 10/2005 | Lin | |
| 2006/0199138 A1 | 9/2006 | Corti et al. | |
| 2008/0254401 A1 * | 10/2008 | Yazdi ........................... 433/18 |

* cited by examiner

*Primary Examiner*—Cris L Rodriguez
*Assistant Examiner*—Eric Rosen
(74) *Attorney, Agent, or Firm*—Rodgers & Rodgers

(57) ABSTRACT

A screw-type orthodontic anchor having an upper member with a pair of slots formed therein with the slots being of different depths. A head portion disposed below the upper member with a collar or cap enveloping the upper member and having a protrusion formed on the inner surfaces thereof which is positioned in a hole extending through the head portion.

8 Claims, 2 Drawing Sheets

ORTHODONTIC ANCHOR

BACKGROUND OF THE INVENTION

In orthodontics, anchors are inserted into the of maxilla or mandible bone. The anchors are screwed into the bone with an upper portion protruding from the gum in order to anchor various orthodontic appliances for the purpose of moving teeth in the desired direction. These types of anchors are independent of the teeth and allow the use of multiple orthodontic devices which are attachable to a single anchor.

BRIEF SUMMARY OF THE INVENTION

An orthodontic anchor for placement in the maxillary or mandible bone includes a body portion with an elongated screw portion extending downwardly therefrom and a hexagonal head portion extending upwardly therefrom. An upper member is secured to the upper surface of the head portion with a pair of grooves formed therein and with one of the grooves being deeper than the other for the reception of one or more rectangular wires. A collar is disposed around the head portion or, alternatively, a cap envelopes the upper member and the head portion with a projection formed on the inner surface of the collar and cap for insertion into a hole formed in the head portion so as to interlock the collar and cap with respect to the anchor.

DETAILED DESCRIPTION OF THE INVENTION

Figure 1:
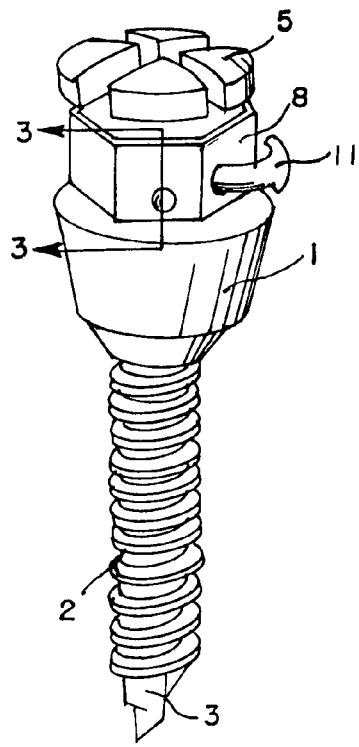
FIG. 1 is a perspective view of the orthodontic anchor according to this invention.
Figure 2:
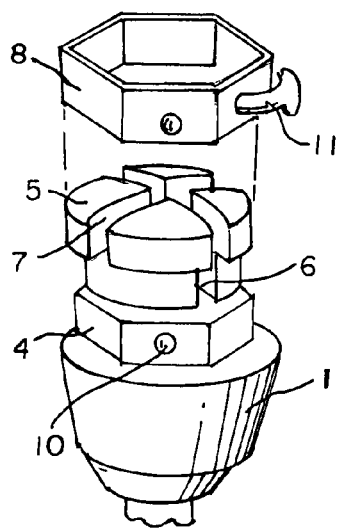
FIG. 2 is an exploded view of the upper portion of the anchor shown in FIG. 1.
Figure 5:
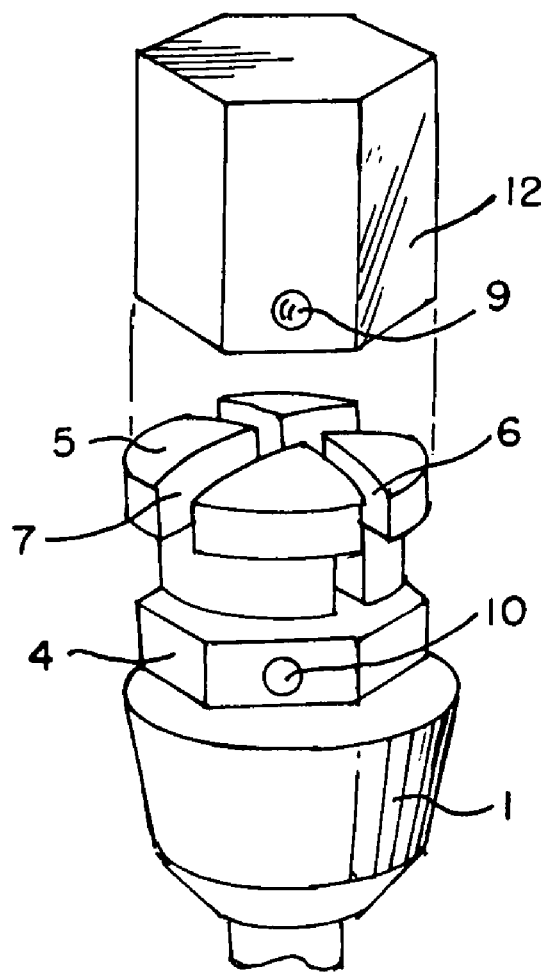
FIG. 5 is an exploded view of the upper portion of the anchor showing a modification of the invention.

In the drawings and with particular reference to FIG. 1, the orthodontic anchor according to this invention is depicted and includes tapered body portion 1 with elongated screw portion 2 integrally joined thereto and extending downwardly therefrom. Self-tapping screw tip 3 is formed on the bottom of screw portion 2 remote from body portion 1. For the purpose of tightening and loosening the anchor, hexagonal head portion 4 extends upwardly from body portion 1. To complete the basic elements of the anchor, slotted upper member 5 is formed on the upper surface of head portion 4 remote from body portion 1. Slotted upper member 5 includes deep groove 6 and shallow groove 7 disposed at right angles, as best shown in FIGS. 2 and 5. Grooves or slots 6 and 7 are formed by a pair of spaced vertical sidewalls which are suitable for the reception and placement of two rectangular wires. Since groove 6 is deeper than groove 7, any undesirable contact between the two rectangular wires is eliminated. The anchor, according to this invention, is also adaptable to the use of only one rectangular wire. Although the size of grooves 6 and 7 may vary in accordance with orthodontic requirements, it has been determined that suitable dimensions are 0.036×0.022 mm for deep groove 6 and 0.028×0.022 mm for shallow groove 7.

For the purpose of attaching various orthodontic appliances to the anchor in accordance with this invention, hexagonal collar 8 is dimensioned to fit snuggly over hexagonal head portion 4. Protrusion 9 is formed on the inner surface of collar 8 and is sized so as to enter hole 10 when collar 8 is positioned around head portion 4 into the position shown in FIG. 1. By this means, collar 8 is securely interlocked with respect to head portion 4 so that undesirable separation therefrom is prevented. Also, hole 10 extends completely through head portion 4 so that an orthodontic wire or other suitable device is attachable to the anchor in the absence of collar 8. In addition, hook 11 extends from collar 8 for the purpose of the attachment of various orthodontic devices such as a wire, spring, elastomeric band, etc.

Figure 3:
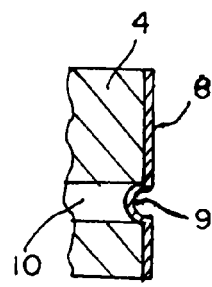
FIG. 3 is a cross-sectional view taken along the line 3-3 in FIG. 1.
Figure 6:
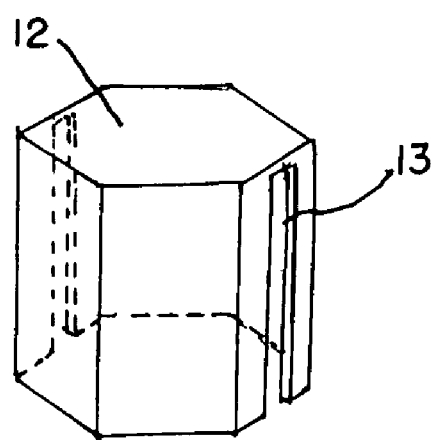
FIG. 6 is a perspective view of a further modification of the orthodontic anchor cap element shown in FIG. 5.

A modification of the orthodontic anchor is shown in FIG. 5 wherein hexagonally-shaped cap 12 is adapted to completely envelope upper member 5 of the anchor and fit snuggly about head portion 4. Projection 9 is formed on the inner surface of cap 12 and is adapted to slide into hole 10 in the same manner as described in connection with the structure shown in FIG. 3. In FIG. 6, multiple slots 13 are formed in the downwardly extending wall of cap 12 which facilitate placement of cap 12 when a rectangular wire is disposed within slot 6 or 7 so that the rectangular wire is disposed within slots 13 when cap 12 is disposed in its fully seated position. Of course, suitable orthodontic tubes and wires are attachable to cap 12 by an suitable means such as welding, glue and the like.

Figure 4:
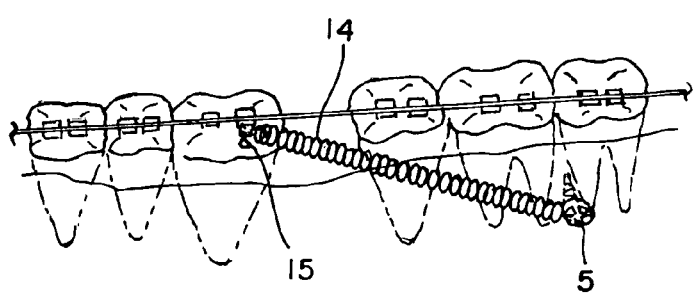
FIG. 4 is an elevational view showing an application of the orthodontic anchor.

In FIG. 4, one application of this invention is shown wherein spring 14 is attached to conventional bracket 15 at one end and to the anchor at the other end. As the patient's tooth realignment progresses, various orthodontic devices can be secured to the anchor and are easily changed without the necessity to relocate the anchor.

In addition, in accordance with this invention, a set including the anchor and collars, which are compatible with a patient's particular requirements, are packaged with a screwdriver in a sterile or nonsterile package. This particular set is suitable for a single application and can be easily ordered online by the orthodontist and simply discarded after use. By this means, extensive conventional orthodontic anchor sets which are expensive and reused are eliminated.

The invention claimed is:

1. An orthodontic anchor comprising a body portion, an elongated screw portion extending downwardly from said body portion, a head portion extending upwardly from said body portion remote from said screw portion, an upper member secured to said head portion remote from said body portion, a pair of U-shaped grooves formed in said upper member, said grooves formed respectively by a pair of spaced vertical sidewalls, said sidewalls of each groove being parallel, said sidewalls having top and bottom edges, said bottom edges of each groove being interconnected by a horizontal bottom, said grooves being open between said top edges, and said bottoms being vertically offset from each other, wherein said bottoms extend perpendicular to the longitudinal axis of said orthodontic anchor.

2. An orthodontic anchor according to claim 1 wherein said grooves are disposed at right angles to each other.

3. An orthodontic anchor according to claim 1 wherein a collar is disposed around said head portion, wherein said head potion is hexagonal, wherein said collar comprises vertical hexagonal sides, and wherein said collar sides are in face contacting relation with said head portion.

4. An orthodontic anchor according to claim 3 wherein a protrusion is formed on the interior of one side of said collar.

5. An orthodontic anchor according to claim 4 wherein a hole is formed in said head portion and said protrusion is adapted to extend into said hole.

6. An orthodontic anchor according to claim 3 wherein a hook extends from said collar.

7. An orthodontic anchor according to claim 1 wherein a cap envelopes said upper member and said head portion.

8. An orthodontic anchor according to claim 7 wherein a pair of oppositely disposed slots are formed in said cap.

* * * * *